United States Patent [19]

Calzi

[11] Patent Number: 4,652,137

[45] Date of Patent: Mar. 24, 1987

[54] CENTRIFUGAL ANALYZER

[75] Inventor: Claudio Calzi, Milan, Italy

[73] Assignee: Allied Corporation, Morris County, N.J.

[21] Appl. No.: 873,866

[22] Filed: Jun. 12, 1986

Related U.S. Application Data

[63] Continuation of Ser. No. 592,520, Mar. 23, 1984, abandoned.

[30] Foreign Application Priority Data

Apr. 13, 1983 [IT] Italy ................................. 20560 A/83

[51] Int. Cl.⁴ ...................... G01N 21/25; G01N 21/90
[52] U.S. Cl. ..................................... 356/427; 356/414
[58] Field of Search ............... 356/409, 414, 427, 436; 422/64

[56] References Cited

U.S. PATENT DOCUMENTS

| | | | |
|---|---|---|---|
| 3,555,284 | 1/1971 | Anderson | 250/218 |
| 3,883,305 | 5/1975 | Hoskins et al. | 23/253 R |
| 4,030,834 | 6/1977 | Bauer et al. | 356/197 |
| 4,061,428 | 12/1977 | Amano et al. | 356/175 |
| 4,202,632 | 5/1980 | Maechtle et al. | 356/427 |
| 4,266,531 | 10/1980 | Tiffany | 356/246 |
| 4,329,061 | 5/1982 | Snook et al. | 356/414 |
| 4,329,062 | 5/1981 | Haar et al. | 356/414 |
| 4,372,683 | 2/1983 | Sternberg | 356/427 X |
| 4,406,547 | 9/1983 | Aihara | 356/414 |

FOREIGN PATENT DOCUMENTS

WO83/384 2/1983 PCT Int'l Appl. .

1438133 6/1976 United Kingdom ................ 356/427

Primary Examiner—Michael R. Lusighan
Attorney, Agent, or Firm—Shlesinger, Fitzsimmons & Shlesinger

[57] ABSTRACT

A centrifugal analyzer has a support for receiving a multicuvette rotor that defines a circumferential array of cuvettes, the analysis regions of the rotor being disposed circumferentially about the periphery of the support when the rotor is on the support. The rotor support is driven in rotation to subject the cuvettes to centrifugal force to position reaction products in respective analysis regions of the cuvettes for analysis, all of the analysis regions being moved along a fixed circular path as the drive means drives the rotor support. A plurality of fixed analysis channels are disposed along the fixed circular path about the periphery of the support, each analysis channel including means for directing radiation into analysis regions as they are moved along the path, and a radiation sensor aligned with the radiation directing means for receiving radiation emitted from analysis regions of the cuvette of the rotor and generating an output signal as a function of the emitted radiation, where each radiation has a well defined wave length. Processor apparatus connected to the plurality of radiation sensors receives concurrently output signals generated by the plurality of radiation sensors while the cuvettes of the rotor are being subjected to centrifugal force, and provides analytical data on reaction mixtures in the rotor cuvette analysis regions in response to the received output signals.

17 Claims, 4 Drawing Figures

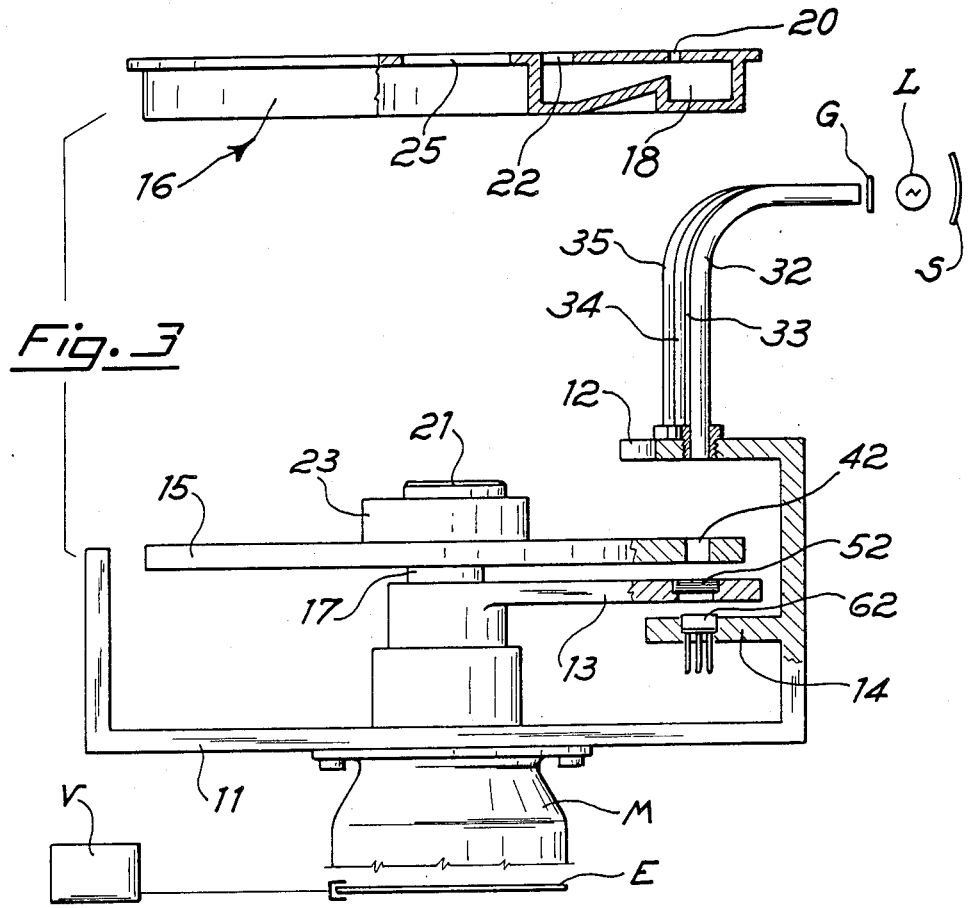
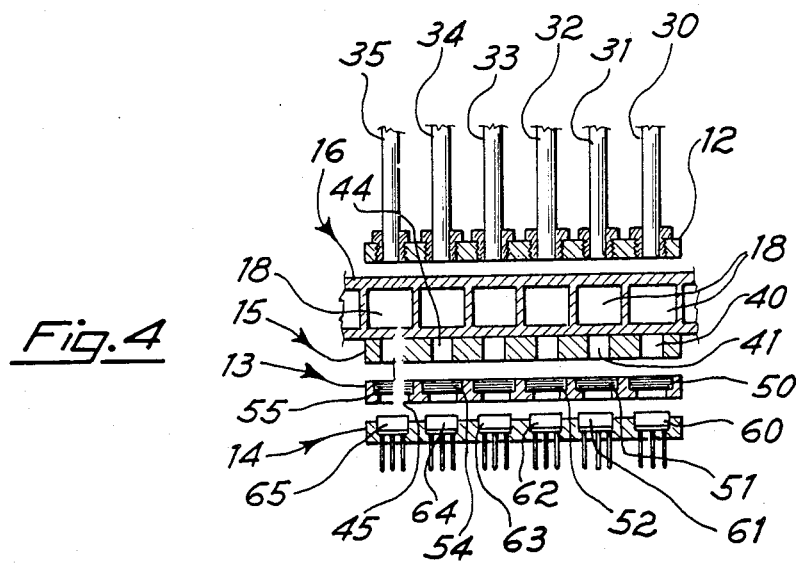

CENTRIFUGAL ANALYZER

This application is a continuation of Ser. No. 592,520 filed Mar. 23, 1984, now abandoned.

This invention relates to analytical systems, and more particularly to centrifugal analyzer systems.

Centrifugal analyzers are useful in performing a variety of analyses, including kinetic and endpoint analyses, by such techniques as absorption, light scattering and fluorescence. In general, such analyzers utilize a multicuvette rotor assembly which has a circumferential array of spaced elongated radially extending cuvettes, each of which has an inner chamber for initially holding a first reactant which frequently is a sample of blood or other biological fluid, and an outer chamber for initially holding one or more different reactants. Divider structure such as a ramp separates the two chambers, and reactants are transferred by centrifugal force to an analysis region at the outer end of the cuvette for mixing and reaction and subsequent analysis of the reaction by photometric or other analysis technique.

Such analyzers may use rotors of the reusable type, as disclosed in Anderson U.S. Pat. No. 3,555,284 for example or of the disposable type as disclosed in Tiffany et al. U.S. Pat. No. 4,226,531 for example. The cuvettes of the rotor disclosed in the Tiffany patent, for example, are loaded successively with automated loading equipment, small quantities of sample (2-20 microliters) typically being loaded into the inner chambers and reagents in quantities of up to two-hundred microliters being loaded into the outer chambers. The loaded cuvette rotor is then transferred to an analyzer for analysis by methods such as photometric, light scattering and/or fluorescence. In a typical analysis sequence, the rotor assembly is first spun at 100 rpm, and then accelerated to about 4,000 rpm in about one second for transferring reactants from the inner chambers and mixing sample and reagent, then braked, and then brought up to about a speed of about 1,000 rpm for analysis. In the analyzer disclosed in the Anderson patent, for example, a single light source and a single photodetector are aligned and the several analytical regions of the cuvette pass between the aligned light source and photodetector for determining the concentrations of a single, particular constituent of the reactant mixtures in the several cuvettes of the rotor. With known centrifugal analyzers, photometric analysis on different parameters of samples requires extended amounts of analysis times and restarts or use of completely different machines In accordance with the invention, there is provided a centrifugal analyzer that has a support for receiving a multicuvette rotor that defines a circumferential array of cuvettes, the analysis regions of the rotor being disposed circumferentially about the periphery of the support when the rotor is on the support. A drive revolves the rotor support to subject the cuvettes to centrifugal force to position reaction products in respective analysis regions of the cuvettes for analysis, all of the analysis regions being moved along a fixed circular path as the rotor support is revolved. A plurality of fixed analysis channels are disposed along the fixed circular path about the periphery of the support, each analysis channel including means for directing radiation into analysis regions as they are moved along the path, and a radiation sensor aligned with the radiation directing means for receiving radiation emitted from analysis regions of the cuvette of the rotor and generating an output signal as a function of the emitted radiation. Processor apparatus connected to the plurality of radiation sensors receives concurrently output signals generated by the plurality of radiation sensors while the cuvettes of the rotor are being subjected to centrifugal force, and provides analytical data on reaction mixtures in the rotor cuvette analysis regions in response to the received output signals.

In preferred embodiments, the analyzer includes fixed frame structure that supports components of the analysis channels in optical alignment; the radiation directing means includes means for transmitting radiation from a single or multiple light source simultaneously on to transparent windows of the same number analysis regions of aligned cuvettes, the radiation sensors are a corresponding plurality of photodetectors, and the drive means includes a motor carried by the fixed frame structure for driving the rotor support, and the analysis channels further include a corresponding plurality of means for limiting the radiation transmitted through the analytical regions to specific wavelengths. Such analyzer permit almost instantaneous measurement through absorbance or transmittance in the sample or samples contained in various cuvettes at different wavelengths, and thereby provides the results of one or more diagnostic profiles on one or more patients.

In a particular embodiment, the radiation directing means includes optical fibers, and the radiation limiting means includes various interference filters. In that analyzer embodiment, optical encoder means supplies an electrical synchronizing signal for the cuvettes to the processor; the radiation source is a lamp that is disposed between a mirror and an athermic filter for supplying radiant energy in both the visible spectra and in the invisible spectra to the analysis channels; and the revolving support has along its peripheral edge as many holes as there are cuvettes in the rotor.

The invention provides analyzer systems capable of carrying out analyses on any number of discrete samples, each one of which requires analysis of a different number of parameters, only limited by the number of cuvettes in the rotor. The analyzer is capable of producing one or more diagnostic profiles on one or more patients. Moreover, it is also possible to carry out bichromatic and polychromatic analyses.

Other features and advantages of the invention will be seen as the following description of a particular embodiment progresses, in conjunction with the drawings, in which:

FIG. 3 is a bottom view of the rotor assembly shown in FIG. 1; and

FIG. 4 is a sectional perspective view showing details of a cuvette in the rotor assembly shown in FIG. 1.

DESCRIPTION OF PARTICULAR EMBODIMENT

Figure 1:
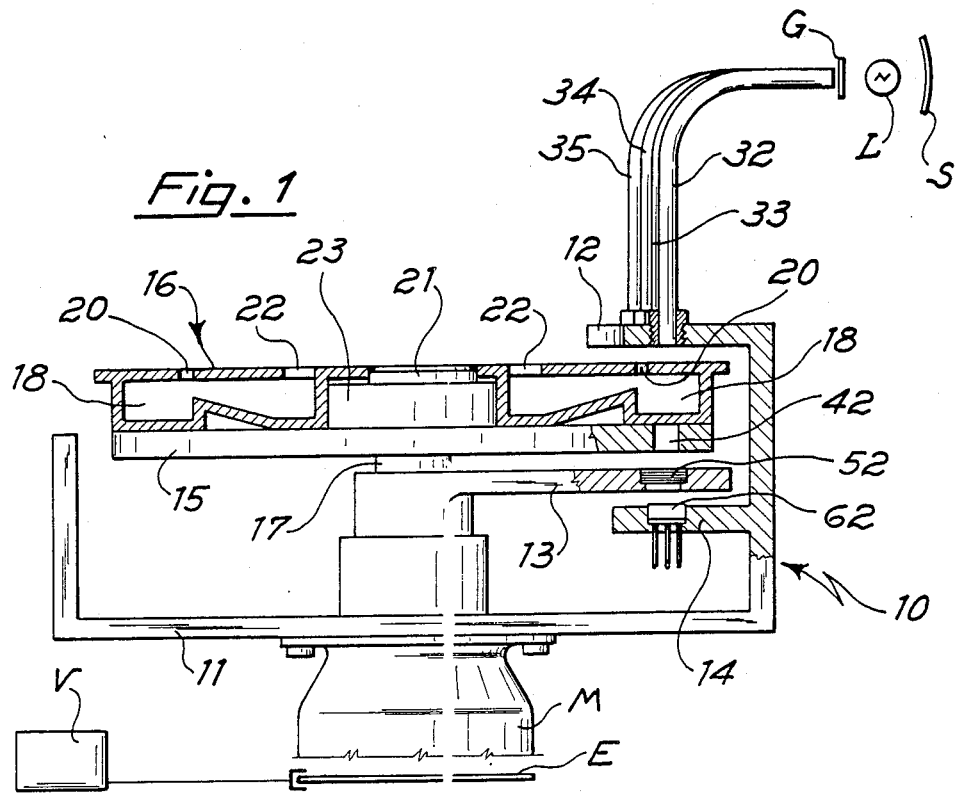
FIG. 1 is a top plan view (with portions broken away) of a multicuvette rotor assembly in accordance with the invention.

Centrifugal analyzer 10 is of the analytical photometer type and comprises a fixed base 11, to which motor M is secured. Motor M drives support 15 for analysis rotor 16 via member 17 which interconnects support 15 and the shaft of motor M.

Six optical fiber channels 30-35 are connected through suitable seals to member 12 that is integral with base 11.

Light source L is disposed between mirror S and athermic filter G for transmitting radiation to optical fibers 30-36.

Analysis rotor 16, which is essentially old and known in the art, incorporates forty or more cuvettes 18, arranged radially side-by-side. Upper holes 20, 22 in correspondence with each cuvette 18, serve for the introduction of the liquid in each of these cuvettes, typically the discrete sample and the necessary chemical reagent optimized for a specific wavelength.

The samples are mixed with the reagents by centrifugal force when motor M drives support 15 to rotate rotor 16.

Holes (40-45 in FIG. 4) at the periphery of support 15 and the same in number as the number of cuvettes in rotor 16 are aligned with the analysis regions of those cuvettes. As support 15 revolves, those holes coincide one by one, with one of the analysis channels optical fibers (30-35 in FIG. 4) or with the other equivalent means provided for transmission of light beams from source L. In fixed alignment with the ends of optical fibers 30-35 are a series of six different interference filters 50-55 supported on fixed arm protrusion 13 and six photodetectors 60-65 supported on fixed flange protrusion 14 of base 11. The several light beams are transmitted, as shown in the figures, by optical fibers 30-35, through the various chemical solutions one by one contained in the cuvettes 18, then through holes (e.g., 40-45) in support table 15 and interference filters 50-55, thereby reaching the corresponding photodetectors 60-65, the photodetectors being aligned with the transparent windows of the analysis regions of cuvette 18, and each optical fiber—photodetector channel being capable of determining the absorbance in the discrete samples contained in cuvettes 18, at a specific wavelength determined by the interference filter of that channel. The resulting electrical signals generated by photodetectors 60-65 are sent to processor V.

Optical encoder E (sketched in FIGS. 1 and 3 as a rectangle) supplies an electrical synchronizing signal for the reading position of each cuvette 18 to processor V.

As the six channels of the analyzer 10 therefore simultaneously analyze chemical solutions contained in the forty cuvettes 18 of rotor 16 for six different parameters, it can be seen that the photometer in accordance with the invention represents a great step forward in its own particular industrial field, as already mentioned earlier on.

Figure 2:
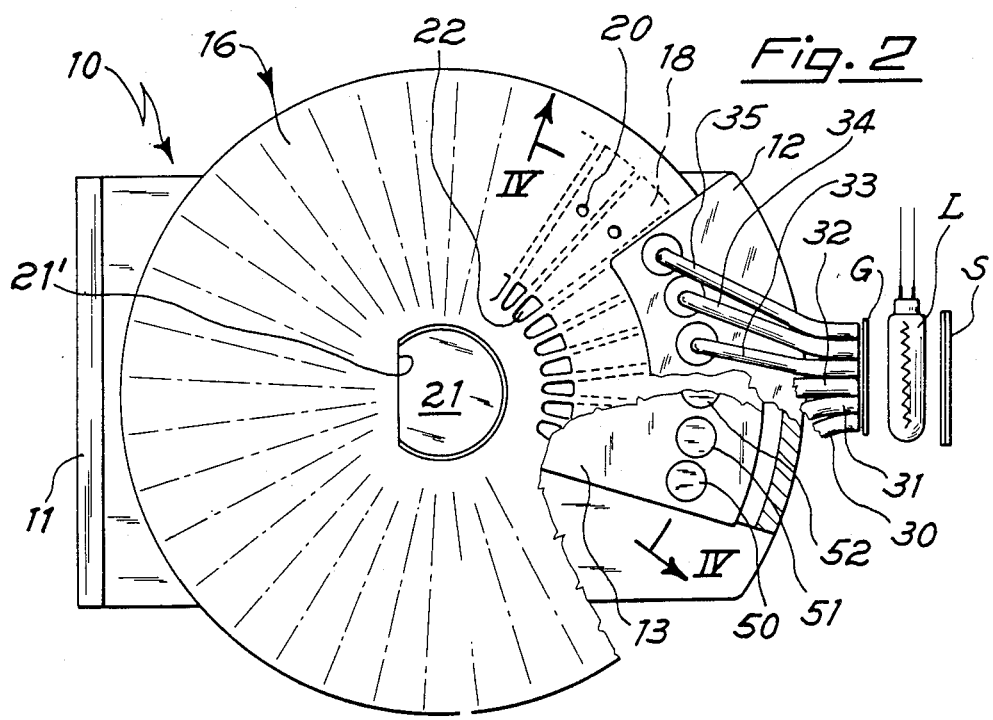
FIG. 2 is a side view (with portions broken away) of the rotor assembly shown in FIG. 1.

By way of completion, in FIGS. 1 and 4 of the drawings, members 21 and 23 are fixed with support 15 for rotor 16, these members being exactly located in the central recess 25 (FIG. 3), and in the one below it, said recesses being incorporated in rotor 16, so that rotor 16 is driven with its support 15. Sectors 13 and support interference filters 50-55 and photodetectors 60-65 respectively. In FIG. 2 the number 21' denotes a surface that provides predetermined orientation of rotor 16 with support 15.

In an analysis sequence, rotor 16 is accelerated to about 4000 rpm by drive motor M during a preliminary run to flow reactant materials contained in the inner chambers up the ramp surfaces and radially outwardly across the ramp crests into the outer chambers. The rotor is then braked to rapidly slow rotor 16 to further enhance mixing of the reactant materials and then successive photometric measurements are made along the several optical axes between optical fibers 30-35 and photodetectors 60-65 while the rotor 10 is being spun at a speed of about 1000 rpm. During the analytical run, centrifugal force drives all of the reactant material in each outer chamber radially outwardly and fills the analytical regions.

It has already been stated that the suitable means for simultaneously transmitting the light beam at multiple points need not only be of optical fibers, but may be of mirrors, or prisms, or other equivalent means. It goes without saying that their number as well as that of the interference filters and of the photodetectors can be greater or lower than that illustrated, and likewise can vary the number of cuvettes provided in the rotor, plus their sectional shape as well as that of the windows for adding the discrete samples and reagents respectively in said cuvettes.

While a particular embodiment of the invention has been shown and described, various modifications will be apparent to those skilled in the art, and therefore it is not intended that the invention be limited to the disclosed embodiment or to details thereof, and departures may be made therefrom within the spirit and scope of the invention.

What is claimed is:

1. In a centrifugal analyzer of the type having a support for receiving and horizontally supporting a multicuvette rotor for rotation about a stationary vertical axis, said rotor containing a circumferential array of cuvettes extending radially outwardly from adjacent the center of said rotor, each said cuvette including structure defining a first chamber region for receiving a first constituent and a loading port through which said first constituent is introduced into said first chamber region, a second chamber region for receiving a second constituent and a second loading part through which said second constituent is introduced into said second chamber region, a divider between said first and second chamber regions, a transfer passage through which said first constituent may flow for forming a reaction product with said second constituent, and an analysis region adjacent the radially outer wall of each cuvette where said reaction product is subjected to analysis, the analysis regions of said rotor being disposed circumferentially about the periphery of said rotor when said rotor is disposed horizontally on said support, and apparatus for driving said rotor support to effect rotation of said rotor about its axis, and to subject said cuvettes to centrifugal force to transfer said first constituents through said transfer passages and form respective reaction products with said second constituents, and to position said respective reaction products in respective analysis regions of said cuvettes for analysis, all of said analysis regions being rotated along a circular path coaxially of said rotor as said driving apparatus drives said rotor support, the improvement comprising means operative during rotation of said rotor for simultaneously analyzing a plurality of said reaction products, said means including a plurality of stationary analysis channels disposed along said circular path adjacent the periphery of said rotor, said analysis channels including means for directing radiation continuously into a predetermined plurality of said analysis regions as said analysis regions are moved along said path, a plurality of stationary radiation sensors equal in number to and aligned with said channels and said radiation directing means for receiving radiation emitted from analysis regions of the cuvette of the rotor, and for generating output signals as a function of said emitted radiation, and processor apparatus connected to said radiation sensors for receiving concurrently said output signals while said driving apparatus is driving said rotor in rotation, and responsive to said output signals to provide analytical data on preselected parameters of the reaction products in said analysis regions.

2. The analyzer of claim 1 and further including fixed frame structure for supporting components of said analysis channels in optical alignment, said radiation directing means including means fixed on said frame structure for transmitting radiation from a single or multiple light source simultaneously on to transparent windows of the analysis regions of said aligned cuvettes, and said analysis channels further include a corresponding plurality of various interference filters fixed on said frame structure, said analyzer permitting almost instantaneous measurement through absorbance or transmittance in the sample or samples contained in various cuvettes at different wavelengths, and thereby providing the results of one or more diagnostic profiles on one or more patients.

3. The analyzer of claim 1 and further including means for supplying an electrical synchronizing signal for said cuvettes and for transmitting said synchronizing signal to said processor.

4. The analyzer of claim 1 and further including a radiation source, said source being arranged between a mirror and an athermic filter for supplying said radiation to said analysis channels.

5. The analyzer of claim 1 wherein said radiation directing means includes optical fibers.

6. The analyzer of claim 1 wherein the light used in said analytical channels contains radiant energy in both the visible spectra and in the invisible spectra.

7. The analyzer of claim 1 wherein said revolving support has along its peripheral edge as many holes as there are cuvettes in said rotor, said holes being aligned with the analysis regions of said cuvettes.

8. The analyzer of claim 1 and further including means for limiting the radiation transmitted through said analysis regions to specific wavelengths.

9. The analyzer of claim 8 and further including fixed frame structure that includes means for supporting components of said analysis channels in optical alignment, said radiation directing means including means fixed on said support means for transmitting radiation from a single or multiple light source simultaneously on to transparent windows of the analysis regions of said aligned cuvettes, said radiation sensors are a corresponding plurality of photodetectors fixed on said support means, and said radiation limiting means includes a corresponding plurality of various interference filters fixed on said support means, said analyzer permitting almost instantaneous measurement through absorbance or transmittance in the sample or samples contained in various cuvettes at different wavelengths, and thereby providing the results of one or more diagnostic profiles on one or more patients.

10. The analyzer of claim 9 wherein said radiation directing means includes optical fibers.

11. The analyzer of claim 10 and further including optical encoder means for supplying an electrical synchronizing signal for said cuvettes and for transmitting said synchronizing signal to said processor.

12. The analyzer of claim 11 and further including a radiation source, said source being arranged between a mirror and an athermic filter for supplying said radiation to said analysis channels.

13. The analyzer of claim 12 wherein the light used in said analytical channels contains radiant energy in both the visible spectra and in the invisible spectra.

14. The analyzer of claim 13 wherein said fixed frame structure includes suitably shaped support protrusion means for supporting said optical fiber, interference filter and photodetector components of said analysis channels in optical alignment.

15. A centrifugal analyzer, comprising
a stand having a pair of vertically spaced arms projecting from one side thereof,
a multicuvette rotor having formed therein a plurality of angularly spaced, radially extending cuvettes, which define a circular array of fluid analysis chambers in said rotor adjacent to its outer peripheral surface,
means removably mounting said rotor on said stand for rotation coaxially about a stationary vertical axis, so that a circumferential marginal portion of said rotor extends into the space between said arms, and so that when said rotor is rotated, said array of analysis chambers is caused to travel in a circular path, a portion of which lies in the space between said arms,
a plurality of analysis channels mounted on said stand to communicate at one end each with a source of radiation, and having the opposite ends thereof fixed to one of said arms in spaced relation to each other, and in confronting relation to said marginal portion of said rotor, and operative during rotation of said rotor to direct radiation from said source onto windows in said analysis chambers as the latter pass between said arms,
a plurality of stationary radiation sensors secured on the other side of said arms to communicate through said windows with the interiors of said analysis chambers as the latter pass between said arms, and operative to produce output signals as a function of the radiation emitted by the fluid contents of said analysis chambers, and
processor apparatus connected to said sensors and responsive to the signals therefrom to provide analytical data on preselected parameters of the contents of said analysis chambers.

16. A centrifugal analyzer as defined in claim 15, wherein said analysis chambers are equal in number to said sensors, and less in number than the analysis chambers in said rotor.

17. A centrifugal analyzer as defined in claim 15, including a plurality of interference filters fixed on said stand to extend between said sensors and said marginal portion of the rotor, and registering with said sensors to filter the radiation emanating from said analysis chambers.

* * * * *